（12） United States Patent
Lönnö

(10) Patent No.: US 6,334,362 B1
(45) Date of Patent: Jan. 1, 2002

(54) DEVICE FOR MEASURING THE SHEARING IN THE CORE OF A SANDWICH STRUCTURE

(76) Inventor: Anders Lönnö, Dragedet 32, SE-139 54 Värmdö (SE)

( * ) Notice: Subject to any disclaimer, the term of this patent is extended or adjusted under 35 U.S.C. 154(b) by 0 days.

(21) Appl. No.: 09/171,860

(22) PCT Filed: Apr. 24, 1997

(86) PCT No.: PCT/SE97/00693

§ 371 Date: Oct. 26, 1998

§ 102(e) Date: Oct. 26, 1998

(87) PCT Pub. No.: WO97/40338

PCT Pub. Date: Oct. 30, 1997

(30) Foreign Application Priority Data

Apr. 24, 1996 (SE) .............................................. 9601566

(51) Int. Cl.⁷ ................................................. G01N 3/24
(52) U.S. Cl. ....................................................... 73/841
(58) Field of Search .......................... 73/841, 846, 847, 73/849, 852, 854, 856, 862.59, 842, 866, 766; 33/534; 264/258; 52/167; 428/113

(56) References Cited

U.S. PATENT DOCUMENTS

| | | | | |
|---|---|---|---|---|
| 3,975,685 A | * | 8/1976 | Bielsten et al. | 73/88.5 R |
| 4,328,621 A | * | 5/1982 | Benjamin | |
| 4,481,902 A | | 11/1984 | Meyer et al. | 116/212 |
| 4,854,175 A | * | 8/1989 | Budhu | 73/841 |
| 4,958,522 A | * | 9/1990 | McKinlay | 73/841 |
| 5,036,709 A | * | 8/1991 | McRae | 73/841 |
| 5,604,314 A | * | 2/1997 | Grahn | 73/628 |
| 5,624,622 A | * | 4/1997 | Boyce et al. | 264/258 |
| 6,205,864 B1 | * | 3/2001 | Vialletel et al. | 73/824 |

FOREIGN PATENT DOCUMENTS

| | | |
|---|---|---|
| DE | 44 02 705 | 8/1995 |
| EP | 0 264 832 | 4/1988 |

* cited by examiner

Primary Examiner—Benjamin R. Fuller
Assistant Examiner—Octavia Davis
(74) Attorney, Agent, or Firm—Jacobson Holman, PLLC

(57) ABSTRACT

The invention relates to a device for measuring the shearing action in the core of a sandwich structure, for instance a hull. The device comprises a sensing means, e.g. a cylindrical rod, and a measuring instrument. The rod is adapted to be inserted into a cylindrical hole which is bored in the hull preferably perpendicular to the surface thereof so as to extend a distance into the core and which has a diameter corresponding to that of the rod. By means of the measuring instrument, an angle between the rod and a reference plane is measured, which is determined by three points on the surface of the hull or the change of this angle when the hull is subjected to a change in load. This angle can be converted into a measure of the current shearing load.

20 Claims, 1 Drawing Sheet

DEVICE FOR MEASURING THE SHEARING IN THE CORE OF A SANDWICH STRUCTURE

FIELD OF THE INVENTION

The invention relates to a device for measuring the shearing action in the core of a sandwich structure. This may comprise sheets or shells of homogeneous or porous materials, composites or the like. The sandwich structure may be used e.g. in a boathull and then usually comprises two hard outer layers and at least one intermediate spacing layer, a core usually made of balsa wood or foamed plastic. The measuring device can be used for static and dynamic measurement of the shearing action in the core material of this hull in order to verify dimensioning while testing or to monitor loads during operation. It can also be used for measurements in laboratory test loads of structural parts such as panels for aeroplanes or vehicles comprising a honeycomb layer as the core. The structures need of course not be panel-shaped. They may be structural parts of an optional form such as frames, reinforcing elements etc.

BACKGROUND ART

For measuring the shearing action in the core material of hulls of sandwich structure, use is in most cases made according to prior art of cylindrical plugs with a $\phi=35$ mm of the core material of the test object and with a length of the thickness of the core layer. In the plugs, foil-type strain gauges are fixed, inclined at an angle of 45 to the axial direction of the plugs. The plugs are arranged in holes bored perpendicularly through one of the outer layers and the core layer. They are attached by gluing in these holes, accurately aligned such that the strain gauges are arranged in a direction in which maximum strain arises. Planes perpendicular to this direction appear when subjecting the core material to shearing load, the planes being inclined at an angle of 45 to the central layer of the core layer and, in for instance rectangular sandwich panels, along a ring located at a varying distance from the panel edge. When the core material cracks owing to too great shear stress, this mostly takes place in such a plane.

The use of such plugs is disadvantageous. The premanufacture and installation of plugs that are not reused is costly, time-consuming and requires especially trained staff. In order that the relatively large holes that are made in the outer layer for the installation should not reduce the strength of the hull in an impermissible manner, the strength of the layer must be reestablished. One way of reestablishing the strength of the layer is by making a cover of the same character as the layer over the plug. It is difficult to ascertain in advance the direction of planes having maximum shear stress, such that the plugs obtain an attachment with a reliable alignment of the strain gauge. The use requires costly calibration and yields poor accuracy. For some core materials, e.g. honeycomb, it cannot be used at all.

DESCRIPTION OF THE INVENTION

Technical Problem

The object of the invention is to provide a device for measuring the shearing action in the core of sandwich structures without the above-mentioned drawbacks. It should be possible to use the device without any extensive preparatory work. Reliable measurements should be possible independently of the alignment of attachment of the device to the test object.

Solution

According to the invention, a device is provided, comprising a sensing means which is adapted to be inserted into a cavity in the core through an opening in the surface of the sandwich structure and abut against at least part of the wall surface that defines the cavity. Moreover, the device comprises an instrument for measuring the angle between the sensing means and a reference plane of the object or the change of this angle. By the measuring operation, a measure of the shearing load in the material adjoining the cavity can be obtained.

FIG. 1 illustrates a core layer from a sandwich panel 1, a longitudinal section being indicated. The panel is assumed to consist of a number of partial layers 2 of the same material and thickness, attached to each other. Through this panel and thus all the partial layers, a cylindrical hole 3 is bored in the longitudinal section, preferably perpendicular to the directions of extent of the panel. A sensing means 4 is inserted in the hole. The means is designed as a cylindrical rod having the same diameter as the bored hole and having such a length as to extend a distance above the top face 5 of the panel.

When the material is subjected to shearing action by, for instance, the lowermost layer of the panel being affected by a force which is parallel with the layer and which is assumed to be directed in the longitudinal direction of the panel to the left in the Figure, while the uppermost layer is kept in position, the central plane of each layer is displaced by the same distance to the left in relation to the closest layer above. Since the hole in each partial layer is displaced together with the partial layer, the rod will follow the movements of the partial layers and thus be turned through an angle 7, which in the ideal case is equal to the shear angle of the shearing action and proportional to the shearing load. On the top face of the uppermost partial layer, i.e. the upper side 5 of the panel, which is here used as a reference plane, an instrument 8 for measuring angular changes of the rod is attached with its symmetry plane in a plane in common with the longitudinal section. The instrument can operate according to some mechanical, optical or electrical principle. In the latter case, it may comprise two electrically operated transducers 9 of prior-art design for contactless measurement at two different levels of the distance from the transducers to the rod 4. By measurements with the aid of these transducers and knowing the vertical distance between the transducers, the angle 7 and consequently the shearing load can be calculated. If at least one more measuring instrument 10 is used, positioned in a direction different from the longitudinal direction of the panel, it is possible, besides measuring an angular change in an optional direction, also to calculate this direction by means of the relationship between the signals of the two measuring instruments.

In case of other shapes of the test object, other reference planes may be used. These need not be located on the outer surface of the object. It may pass, for instance, through three points lowered into the material, the shearing action of which is to be measured. The shaped of the sensing means as well as that of the cavity are not restricted to the shape in the above example. If the means is mounted for turning in e.g. a device connected to the measuring instrument, the means would need to be in contact with the boundary surface of the cavity in a single point only. The contact may then by maintained with a spring assembly on the sensing means. Such resilience is appropriate also for the purpose of taking up lost motion for better accuracy.

Advantages

According to the invention, an inexpensive and easily applicable device is provided, which without any extensive preparatory work yields good values of the shearing action in the core of a sandwich structure and the direction of the shearing action. The hole for the rod and small fixing screws, if any, for the device is much smaller than the holes which are normally made in the hull for cable lead-ins, screws for fixing various kinds of accessories and the like. Therefore, much less damage is caused to the test objects in these measurements compared with measurements according to prior art. By the measuring instrument not being sealed in the test object, it is readily accessible for service and check-up, which is important in long-term measurements in which the measuring accuracy of the plugs may be reduced. Moreover, this results in the device being reusable, which reduces the measuring costs.

DESCRIPTION OF THE DRAWING

A preferred embodiment will be described in more detail with reference to FIG. 2.

DESCRIPTION OF THE PREFERRED EMBODIMENT

In the preferred embodiment, a simplified device according to the invention is used. The device can be used merely for objects having rigid outer layers such as a hull of sandwich structure. By letting the sensing means, the rod, be mounted in one of the outer layers, the measuring instruments, which are both attached to the same outer layer, can be each provided with a single transducer. As a result, the cost of the transducers and the associated electronic assembly will be about half of the cost in the above-mentioned example.

Figure 2:
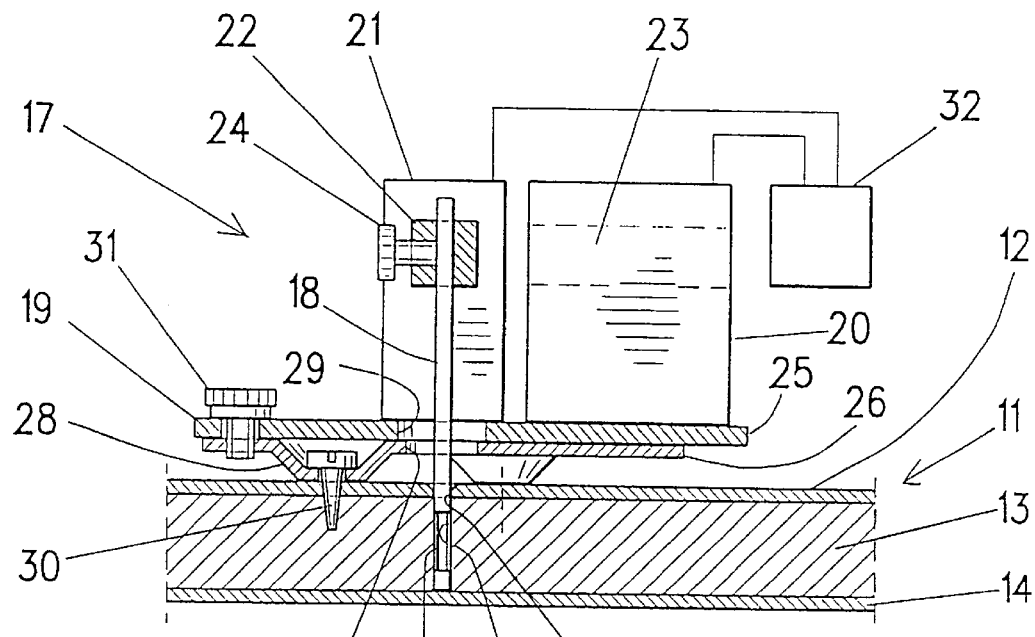
FIG. 2 is a plan view of a preferred embodiment of the invention for measuring the shearing action in the core of a plastic hull of sandwich structure.
Figure 1:
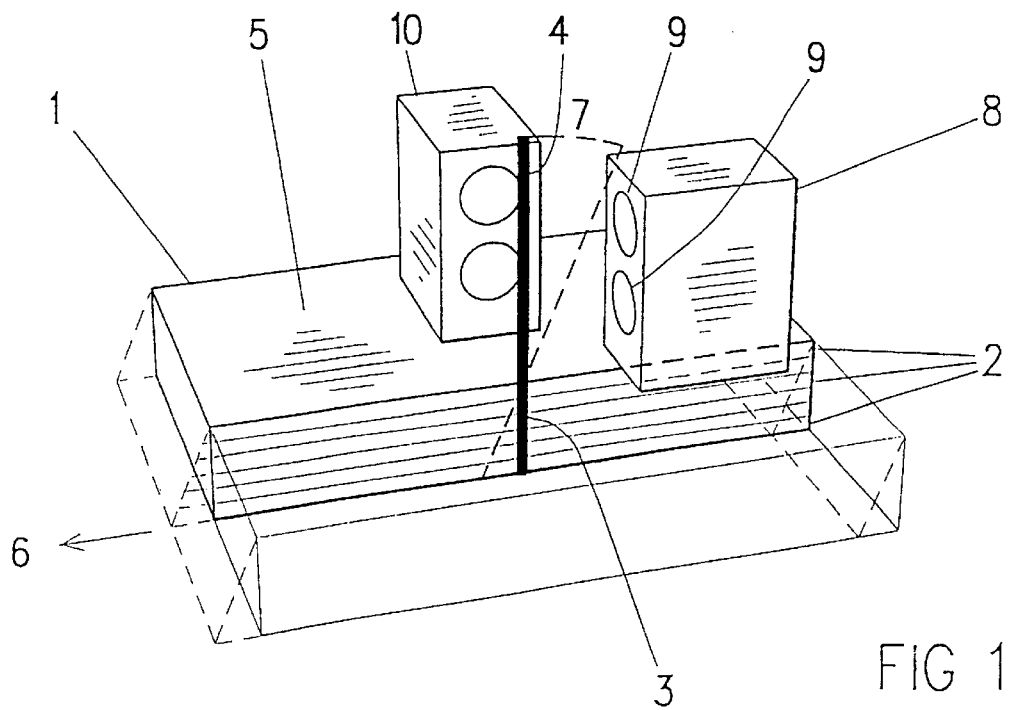
FIG. 1 is a schematic view of the device together with a sheet-shaped panel of core material.

A portion of the bottom of the hull is designated in FIG. 2. The portion is a sandwich structure consisting of an internal outer layer 12 of a rigid reinforced plastic, a core layer 13 of an expanded plastic, and an external outer layer 14 of the same kind as the internal outer layer. A cylindrical guide hole having a diameter of 3–4 mm is bored through the internal outer layer and the core layer. The thus resulting through holes in the internal outer layer and the core layer are designated 15 and 16.

The measuring instrument 17 comprises as main parts a sensing means having a rod 18 and a device 22 for determining the position of the rod, a base 19 and one or, as shown in the Figure, two measure-indicating means 20, 21. The rod 18 is a cylindrical metal rod having a diameter corresponding to the diameter of the guide hole and such a length as to permit insertion into the guide hole 15, 16 all the way down to the external outer layer 14 and projection up from the internal outer layer a distance that is determined by the demands as to the function of the measuring instrument. If for instance "honeycomb" is used as spacing material, the lower end of the rod must be fixed, for example by means of an elastic glue, to an expanding plug which is inserted down to the bottom of the hole or by the hole being bored also through the other outer layer.

The measure-indicating means each comprise a contactless distance transducer 23 (the farther transducer is concealed in the Figure). The position-determining device is a cubic device 22 attached to the projecting part of the rod and adapted to improve the function of the distance transducers. It has a cylindrical hole, in which the rod is inserted, and a clamping screw 24 for attaching it to the rod.

The base 19 is stable fixing plate 25 of metal, on the upper side of which the measure-indicating means are attached, and a base disc 26 of thick metal sheet. The base disc is formed with a central hole 27 and three supports 28 pressed into the metal sheet and equidistantly spaced along a circle which is concentric with the base disc. The fixing plate has a hole 29, through which the rod can extend and move freely, just like through the hole 27 of the base disc. The base disc is attached to the internal outer layer of the hull by means of three conically threaded fixing screws in the supports formed with holes. Only one of these screws 30 is shown in the Figure. The fixing plate is laterally adjustably fixed on the top of the base disc by means of three adjusting screws which are screwed into the base plate and of which only one 31 is shown.

From the measure-indicating means 20 and 21, wires are laid to an electronic assembly 32 which is adapted to control the measurement, convert input signals into angular magnitudes and present these magnitudes.

Use of the Device

After boring the hole through the internal outer layer and the core layer, the edge of the hole 15 of the outer layer is burred such that the hole can act as pivot bearing for the rod inserted into the hole. The base disc 26 is fixed with the supports 28 to the outer layer by means of the fixing screws 30 concentrically with the rod, whereupon the fixing plate 25 with the measure-indicating means is mounted on the base disc, and the position-determining device 22 is pushed onto the rod. The electronic assembly is started, and by means of values obtained therefrom the fixing plate is adjusted in lateral direction and the position-determining device on the rod is adjusted in vertical direction and in the direction of rotation, such that these obtain current starting positions before the measuring operation is begun. The instrument can be calibrated, for instance by pulling a sleeve of prior-art design in a controlled manner onto the position-determining device.

In the contact points which the three supports have with the outer layer, it is possible to image the reference plane that is used in the measuring operation. A reference plane which is favourable for the measuring accuracy also if the structure is subjected to bending is obtained if these contact points are essentially equidistantly spaced from the rod and the instrument is arranged with e.g. two supports in a plane parallel with the plane of bending. To prevent a nonlinear shearing action of the core from causing bending of the rod and resulting errors of measurement, the rod has a portion 33 of reduced diameter at the level of the central part of the core.

If the device is provided with only one measure-indicating means, this may be turned about an axis normal to said reference plane and extending through the opening of the cavity to a position where the shear angle is at a maximum. The turning can be accomplished if e.g. the holes in the fixing plate 25 for the fixing screws 31 are in the form of a circular arc.

In a four-point tensile test, the device has produced good results. The relationship between the output voltage of the used contactless distance meter and the shear strain has been linear. As a result, accurate measurements can be carried out without extensive calibrations.

What is claimed is:

1. A device for measuring shearing action of a core material of a sandwich structure, comprising a mechanically-working sensing element made of a rigid non-brittle material and a measuring instrument, the sensing element being inserted into a cavity in the core material through an opening in a surface of the sandwich structure and abutting a boundary surface of the cavity, the measuring instrument being at least partially located exterior to said core material and measuring an angle between the sensing element and an imaginary reference plane defined by at least three points in the sandwich structure, said angle being dependent on said shearing action within said core material and indicating shearing load.

2. The device as claimed in claim 1, wherein the cavity comprises a cylindrical part, and the sensing element comprises a cylindrical portion which is inserted with a fit into the cylindrical part of the cavity.

3. The device as claimed in claim 2, wherein the cavity is cylindrical, and a part of the sensing element that extends down into the cavity is cylindrical with a diameter which corresponds to that of the cavity except at a neck having a reduced diameter at a level of a central part of the core.

4. The device as claimed in claim 1, wherein the measuring instrument comprises a transducer for measuring a distance to the sensing element, the transducer arranged in a plane in which the sensing element moves as a shearing load is changed.

5. The device as claimed in claim 1, wherein the device comprises two transducers for measuring distances to the sensing element, the transducers being arranged in separate planes comprising an axis through the sensing element.

6. The device as claimed in claim 1, wherein the device comprises two transducers which measure distances to the sensing element at two different levels thereof.

7. The device as set forth in claim 1, said measuring device measuring said angle after shearing of the core material.

8. The device as set forth in claim 1, said measuring device measuring a change in said angle from before shearing to after shearing.

9. A device for measuring shearing action of a core material within a sandwich structure, comprising:

a rigid non-brittle sensing element having a portion inserted in fitted engagement with a cavity in the core material through an opening in an outer surface layer of the sandwich structure, said sensing element defining a first angle with respect to a reference plane, and said sensing element being tilted in response to shearing of the core material which exerts physical shear force against said portion of said rigid sensing element fitted in said core material to define a second angle between the sensing element and the reference plane;

measure indicating means for measuring said first and second angles, said measure indicating means being attached to said sandwich structure in at least three points and said reference plane being defined by three of these points; and control means for receiving signals indicating said first and second angles.

10. The device as set forth in claim 9, wherein said reference plane is parallel to or coincident with said outer surface layer.

11. The device as set forth in claim 9, wherein said first angle is approximately 90°.

12. The device as set forth in claim 9, wherein said measure indicating means is rotatable about an axis normal to said reference plane and extends through the opening to a position where the second angle is at a maximum value, the position where the second angle is maximized corresponding with a main direction of the shearing action.

13. The device as set forth in claim 9, wherein the core material is a non-magnetic honeycomb spacing material and the sensing element includes a rod having a lower end fixed at a bottom of the cavity.

14. The device as set forth in claim 9, wherein said control means includes an electronic assembly wired to said measure indicating means.

15. The device as set forth in claim 14, wherein said electronic assembly calculates a shearing load from the measured angles.

16. The device as set forth in claim 9, wherein the sensing element includes a rod having a lower end fixed at a bottom of the cavity and extending upward to protrude from the outer surface layer, said measure indicating means including a transducer for measuring a distance from the measure indicating means to the sensing element.

17. The device as set forth in claim 16, said measure indicating means including two transducers for respectively measuring distances to said sensing element at two different levels.

18. The device as set forth in claim 9, said measure indicating means including a first measure indicating element and further comprising a second measure indicating element for measuring angles in two directions, a main direction of the shearing action being calculated by said control means using a response from each of said first and second measure indicating elements.

19. The device as set forth in claim 12, wherein said control means includes an electronic assembly wired to said measure indicating means for calculating a shearing load from the measured angles, said shearing load being determined with the measure indicating means in the position wherein the second angle is maximized.

20. A device for measuring shear of a core material within a sandwich structure, comprising:

a rigid sensing element having a portion inserted in fitted engagement with a cavity in the core material through an opening in an outer surface layer of the sandwich structure, said sensing element defining a first angle with respect to said outer surface layer, and said sensing element remaining unbent while being physically tilted in response to shearing of the core material which exerts shear force against said portion of said rigid sensing element fitted in said core material to define a second angle between said sensing element and said outer surface layer;

a first measure indicating element for measuring said first and second angles, said first measure indicating element being attached to said sandwich structure in at least three points and said outer surface layer being defined by three of these points;

a second measure indicating element for measuring said angles from a second direction; and an electronic assembly for receiving angle information from said first and second measure indicating elements and for calculating a shearing load and a main direction of shearing action from said angle information.

* * * * *